United States Patent
Stanjek et al.

(10) Patent No.: US 6,440,328 B1
(45) Date of Patent: Aug. 27, 2002

(54) PREPARATION OF ACRYLATED LIQUID-CRYSTALLINE COMPOUNDS

(75) Inventors: Volker Stanjek, München; Wolfram Schindler, Unterhaching; Thomas Kammel; Norman Häberle, both of München, all of (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/552,448

(22) Filed: Apr. 18, 2000

(30) Foreign Application Priority Data

Apr. 27, 1999 (DE) .......................... 199 19 153

(51) Int. Cl.[7] .................. C09K 19/20; C09K 19/12; C07C 69/76
(52) U.S. Cl. .................. 252/299.67; 252/299.64; 252/299.65; 560/86; 560/89; 560/108; 560/109
(58) Field of Search .............. 252/299.01, 299.64, 252/299.65, 299.67; 560/86, 89, 108, 109

(56) References Cited

FOREIGN PATENT DOCUMENTS

| DE | 646 820 | 6/1937 |
|---|---|---|
| DE | 197 16 822 A1 | 10/1998 |
| EP | 0 648 827 A1 | 4/1995 |
| FR | 1 211 945 | 3/1960 |
| GB | 2 297 549 | 8/1996 |
| WO | WO95/07879 | 3/1995 |
| WO | WO96/23036 | 8/1996 |
| WO | WO96/24647 | 8/1996 |
| WO | WO98/47979 | 10/1998 |

OTHER PUBLICATIONS

Polym. Prep. 30 (2), 462–463, 1989.
J. Chem. Tech. Biotechnol, 41, 1988, p. 45–49.
Derwent Abstract Corresponding To JP–A 61–286346 (An 1987–027588).
Derwent Abstract Corresponding To DE–A 197 16 822 (An 1998–569505).
International Search Report—Aug. 3, 2000.

*Primary Examiner*—Shean C. Wu
(74) *Attorney, Agent, or Firm*—Brooks & Kushman P.C.

(57) ABSTRACT

The invention relates to a one-step process for the preparation of acryloyl group-containing liquid-crystalline monomers of the general formula (1)

$$(Z-Y^1-A^2-Y^2-)_m M(-O-A^1\text{-acrylate})_n \quad (1)$$

in which mesogenic alcohols of the general formula (2)

$$(Z-Y^1-A^2-Y^2-)_m M(OH)_n \quad (2)$$

are reacted with esters of 3-chloropropionic acid of the general formula (3)

$$ClPr-A^1-X \quad (3)$$

with elimination of HCl, where acrylate is an acrylate radical,

ClPr is a 3-chloropropionate radical, $A^1$ are identical or different alkyl chain spacers having 2–20 carbon atoms, in which the carbon chain may be interrupted by non-adjacent ether, thioether, or imino groups, $A^2$ are radicals $A^1$ or single chemical bonds, M is a mesogenic group, X is a leaving group, Z are alkyl radicals or crosslinkable groups, $Y^1$ and $Y^2$, independently of one another, are a single chemical bond, —O—, —S—, —O—CO—, —CO—O—, —O—CO—O, —CO—NR$^1$—, —NR$^1$—CO—, —O—CO—NR$^1$—, —NR$^1$—CO—O— or —NR$^1$—CO—NR$^1$—, $R^1$ is hydrogen or a $C_1$–$C_4$-alkyl radical, n is 1, 2, 3 or 4, and m is 0, 1, 2 or 3.

20 Claims, No Drawings

PREPARATION OF ACRYLATED LIQUID-CRYSTALLINE COMPOUNDS

TECHNICAL FIELD

The invention relates to a one-step process for the preparation of liquid-crystalline monomers containing acryloyl groups.

BACKGROUND ART

In general, the production of three-dimensional networks having a desired optically anisotropic property profile requires crosslinkable liquid-crystalline monomers in which the mesogenic units and the crosslinkable groups are separated front one another by spacer units. The incorporation of the spacers increases the mobility of the acrylic groups and is vital for achieving a sufficiently high degree of crosslinking. In addition, the liquid-crystalline phase of the monomers can be positively affected by the choice of suitable spacer lengths.

Owing to the necessity for a spacer, however, the desired monomers cannot be obtained by simple (meth)acrylation of the mesogenic alcohols, which are usually readily accessible. In some cases, significantly more complex synthetic routes must be followed here. It is in many cases favorable for the spacer to be bonded to the mesogenic unit via an ether bond. The corresponding compounds are particularly advantageous owing to their relatively good synthetic accessibility, their chemical stability, but in particular owing to their frequently very advantageous liquid-crystalline property profile.

The literature therefore describes numerous synthetic routes which in principle are suitable for the synthesis of crosslinkable mesogens containing corresponding spacers. However, these synthetic routes are without exception afflicted with specific disadvantages or limitations. Thus, for example, WO 96/24647 and WO 96/23036 describe processes in which a mesogenic diol is first reacted with an ω-haloalcohol. The resultant intermediate is subsequently esterified using (meth)acryloyl chloride to give the finished product. There are numerous problems associated with this process. First, the alcohols produced as intermediates generally have poor solubility properties, making not only their preparation, but also their isolation and purification, very complex. Second, the ω-haloalcohols required as starting materials are relatively expensive compounds which frequently cannot be produced on an industrial scale. This synthetic route is therefore disadvantageous for commercial production.

In another process, described, for example, in WO 98/47979 and EP 0 648 827, the starting materials are ω-halo(meth)acryloylalkanes, which can be reacted with a mesogenic monol or diol in a single step to give the desired end product. The labor-intensive isolation of a mesogenic intermediate containing hydroxylated spacer units is not necessary here. However, a disadvantage of this process is the preparation of the required ω-halo(meth)acryloylalkanes starting materials, since these compounds have a strong tendency toward undesired polymerization, and are therefore virtually impossible to handle without a stabilizer. The tendency toward polymerization is particularly pronounced in the case of the acryloyl compounds, and thus their synthesis and purification is only possible with difficulty in virtually all cases. In addition, scale-up of such reactions to an industrial scale requires complex safety precautions.

Finally, the literature also describes a number of preparation processes which follow a completely different strategy. However, it is common to all these that they can without exception only be achieved by multistep, and therefore very complex, synthetic routes.

DISCLOSURE OF INVENTION

The present invention has the object of overcoming the disadvantages of the known synthetic routes and of providing a process by means of which crosslinkable mesogens containing spacer-bonded acrylic groups can be prepared simply and in an acceptable manner with respect to the reaction and safety. This process can prepare the desired crosslinkable mesogens economically and in a single step.

BEST MODE FOR CARRYING OUT THE INVENTION

The invention relates to a one-step process for the preparation of acryloyl group-containing liquid-crystalline monomers of the general formula (1)

$$(Z-Y^1-A^2-Y^2-)_mM(-O-A^1\text{-acrylate})_n \qquad (1)$$

in which mesogenic alcohols of the general formula (2)

$$(Z-Y^1-A^2-Y^2-)_mM(OH)_n \qquad (2)$$

are reacted with esters of 3-chloropropionic acid of the general formula (3)

$$ClPr-A^1-X \qquad (3)$$

with elimination of HCl, where acrylate is an acrylate radical,

ClPr is a 3-chloropropionate radical, $A^1$ are identical or different alkyl chain spacers having 2–20 carbon atoms, in which the carbon chain may be interrupted by non-adjacent ether oxygen atoms, thio-ether sulfur atoms, or imino groups, $A^2$ are radicals $A^1$ or single chemical bonds, M is a mesogenic group, X is a leaving group, Z are alkyl radicals or crosslinkable groups, $Y^1$ and $Y^2$, independently of one another, are a single chemical bond, —O—, —S—, —O—CO—, —CO—O—, —O—CO—O, —CO—NR$^1$—, —NR$^1$—CO—, —O—CO—NR$^1$—, —NR$^1$—CO—O— or —NR$^1$—CO—NR$^1$—, $R^1$ is hydrogen or a $C_1$–$C_4$-alkyl radical, n has a value of 1, 2, 3 or 4, and m has a value of 0, 1, 2 or 3.

The process according to the invention starts from a mesogen of the general formula (2) containing one or more free hydroxyl groups. The invention is based on the discovery that, in a single synthetic step, the ether bond between the mesogenic alcohol of the general formula (2) and the 3-chloropropionate of the general formula (3) can be formed with elimination of the leaving group X and simultaneously the acryloyl group can be liberated from the chloropropionate group by elimination of an HCl molecule.

The process according to the invention is highly suitable for the preparation of mesogens containing 1 to 4 spacer-bonded acrylic groups, where n has a value of from 1 to 4, in particular 2. The desired mesogen of the general formula (1) may be prepared in only a single synthetic step from readily accessible starting materials. Further, the process according to the invention allows a synthesis concept scheme in which the acrylic acid functionality of the 3-chloropropionate precursors of the general formula (2) are masked. The demasking is delayed until during the final reaction step of the entire mesogen synthesis, the described etherification of a mesogenic alcohol. Thus, unpolymerizable starting materials are exclusively employed in the synthesis sequence for the preparation of acrylated mesogens of the general formula (1), and in addition no polymerizable intermediates are formed. The performance of the individual synthetic steps, but in particular the handling of the intermediates, is thus significantly simplified.

A further advantage of the process according to the invention consists in the fact that the esters of the required 3-chloropropionic acid starting materials of the general formula (3) can easily be prepared by reaction of suitable alcohols or cyclic ethers with 3-chloropropionyl chloride, a chemical produced on a large industrial scale. Direct esterification of the free 3-chloropropionic acid, for example by azeotropic esterification using the targeted alcohol derivatives, is also possible. The reaction according to the invention is thus also extremely valuable for industrial applications.

The process according to the invention is suitable for the preparation of any desired liquid-crystalline compounds containing one or more spacer-bonded acrylic groups of the general formula (1). It is preferably employed for the preparation of liquid-crystalline bisacrylates of the general formula (1) in which m is 0 and n is 2 by reaction of a mesogenic diol of the general formula (2) in which m is 0 and n is 2, with 2 equivalents of a compound conforming to the general formula (3). Use of mixtures of a plurality of compounds conforming to the general formula (3) also allows the preparation of stoichiometric mixtures of symmetrical and asymmetrical bisacrylates. Preferably, only one compound of the general formula (3) is employed.

Furthermore, the process according to the invention can also be employed for the conversion of liquid-crystalline alcohols which already contain crosslinkable groups of the general formula (2) in which m is greater than 0 and Z is a crosslinkable group. The process can also be utilized for the preparation of mesogens containing two different crosslinkable groups and/or spacers, in which case, in the general formulae (1) and (2), m is 1, n is 1 and Z is a crosslinkable group.

Suitable radicals M are all known mesogenic groups. M preferably conforms to the general formula (4)

(—T—Y³)ᵣ—T—     (4)

in which

T are divalent saturated or unsaturated, isocyclic or heterocyclic, substituted or unsubstituted hydrocarbon radicals having 5–20 carbon atoms, preference being given to benzyl, cyclohexyl and naphthyl radicals, Y³ is a single chemical bond, —O—, —S—, —O—CO—, —CO—O—, —O—CO—O—, —CO—NR²—, —NR²CO—, —O—CO—NR²—, —NR²—CO—O—, —NR²—CO—NR²—, —CH₂—O—,—O—CH₂—, —CH=N—, —N=CH— or —N=N—, R² is hydrogen or a C₁–C₄-alkyl radical, and r has a value of 0, 1, 2, 3 or 4, particularly preferably 1 or 2.

In the case where r is greater than 0, the radicals T may be identical to or different from one another, as may the bridging radicals Y³. The radicals T can also be more highly substituted, for example by C₁–C₄-alkyl groups, fluorine, chlorine, bromine, cyano, hydroxyl, (alkyl)amino or even nitro groups. Particularly preferred radicals T are benzyl and cyclohexyl groups, which may, if desired, carry further substituents.

Particular preference is given to mesogenic groups M which conform to the structural formula (5) or (6)

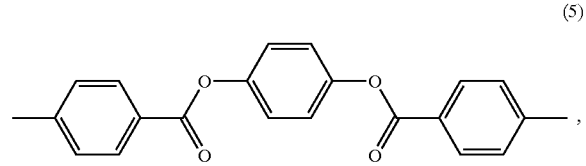

(5)

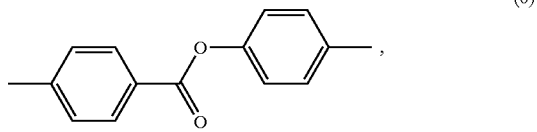

(6)

where each ring can carry one or more identical or different substituents.

Particularly preferred mesogenic diols of the general formula (1) conform to the general formula (7) or (8)

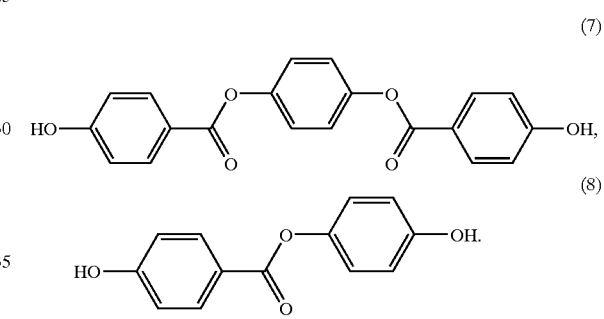

(7)

(8)

These compounds are readily accessible via known synthetic routes from hydroquinone and p-hydroxybenzoic acid or from substituted derivatives of these compounds, as described, for example, in *Polym. Prep.* 30 (2), 462–3, 1989.

The alkyl radicals Z in the general formulae (1) and (2) are preferably C₁–C₄-alkyl radicals. The crosslinkable groups Z can be all groups known to those skilled in the art. Preferred groups Z are alkenyl groups, such as vinyl, 2-methylvinyl, and allyl groups, and alkynyl groups and epoxy groups.

The leaving group X in the general formula (3) can be any group known to the person skilled in the art. Preference is given to halogens and sulfonic acid derivatives, where the latter, such as, for example, triflate of the formula (10), can also contain fluorine-containing radicals. The formulae (9)–(13)

(9)

(10)

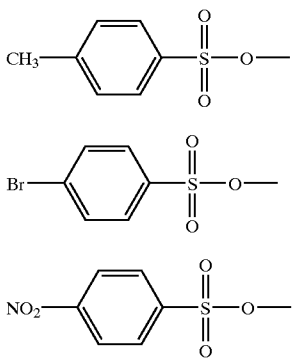

are non-limiting examples of preferred sulfonic acid radicals of this type.

Particularly preferred leaving groups X are chlorine and bromine leaving groups, in which case it is advantageous to carry out the etherification according to the invention in the presence of catalytic amounts of potassium iodide.

For the preparation of suitable compounds of the general formula (3), an extremely extensive repertoire of different processes is available to the chemist. The simplest reaction schematically starts from an ω-haloalcohol, which is reacted with 3-chloropropionyl chloride to give the corresponding ester (X is halogen). Owing to the restricted availability of inexpensive ω-haloalcohols, however, this route is only in exceptional cases of industrial interest.

It is generally preferably here to start with an alkanediol. The alkanediols can be reacted, for example, with 3-chloropropionyl chloride under suitable conditions to give the corresponding 3-chloropropionic monoesters. Esterification of the still-free hydroxyl function in the latter using sulfonyl chlorides enables the simple preparation of activated sulfonic acid derivatives of the general formula (3) in which X is a sulfonic acid derivative.

It is also possible to replace the free hydroxyl group in the above 3-chloropropionic monoester by halogen atoms, for example by reaction with thionyl chloride. The compounds which can be prepared in this way are likewise suitable as starling material of the general formula (3) in which X is a halogen atom.

A particularly efficient and elegant reaction for the preparation of the compound of the general formula (3) is the ring opening of cyclic ethers, such as tetrahydrofuran, by means of 3-chloropropionyl chloride. 4-chlorobutyl 3-chloropropionate is prepared in this manner in only a single, very simple reaction step from extremely inexpensive starting materials.

In the examples below, unless stated otherwise in each case, all amounts and percentages are based on the weight, all pressures are 0.10 Mpa (abs.) and all temperatures are 20° C.

EXAMPLE 1

Preparation of 4-Chlorobutyl 3-Chloropropionate 89.4 ml (114.2 g, 0.9 mol) of 3-chloropropionyl chloride are dissolved in 160 ml of cyclohexane. 613 mg (4.5 mmol) of zinc chloride are added, and the resultant suspension is blanketed with nitrogen. The mixture is subsequently heated to boiling, and 80.4 ml (71.4 g, 0.99 mol) of THF are slowly added dropwise with good stirring. The reaction proceeds very exothermically. The rate of addition of THF should be regulated so that the reaction mixture boils uniformly even without any external heat supply. When the addition of the THF is complete, the mixture is refluxed with stirring for a further 30 minutes.

For work-up, the mixture is allowed to cool to room temperature and is washed with 80 ml of NaOH solution (5% strength) and twice with 80 ml of distilled water. Cyclohexane and residual water are subsequently removed at 60° C. under a partial vacuum, and the product is purified by distillation (84° C. at 1 mbar).

Yield: 164.6 g (92% of theory).

EXAMPLE 2

Preparation of Hydroquinone bis[4-(4-Acryloyloxybutoxy)benzoate]

292 g (2.1 mol) of potassium carbonate, 5 g (30 mmol) of potassium iodide and 0.4 g (1.5 mmol) of 2,6-di-t-butyl-4-(N,N-dimethylaminomethyl)phenol as stabilizer are suspended in 250 ml of N-methyl-2-pyrrolidinone. 105.1 g (0.30 mol) of hydroquinone bis(hydroxybenzoate) are subsequently added with good stirring. When the reaction temperature of 100° C. has been reached, 144.0 g (0.722 mol) of 4-chlorobutyl 3-chloropropionate are added dropwise. The mixture is stirred at this temperature for a further 4 hours.

For work-up, the reaction mixture is cooled to 80° C., and 300 ml of xylene are added. The mixture is washed at this temperature once with 400 ml of water, once with 250 ml of water and a further twice with 50 ml of water. The organic phase is subsequently dried by azeotropic distillation of about 50 ml of xylene in a partial vacuum. The clean product crystallizes out on cooling to 15° C.

Yield: 135.5 g (75% of theory).

EXAMPLE 3

Preparation of 4-(4-Acryloyloxybutoxy)phenol 4-(4-Acryloyloxybutoxy)benzoate 110.4 g (0.8 mol) of potassium carbonate, 1.7 g (10 mmol) of potassium iodide and 0.2 g (0.7 mmol) of 2,6-di-t-butyl-4-(N,N-dimethylaminomethyl)phenol as stabilizer are suspended in 120 ml of N-methyl-2-pyrrolidinone. 23.0 g (0.10 mol) of hydroquinone mono(4-hydroxybenzoate) are subsequently added with good stirring. When the reaction temperature of 100° C. has been reached, 59.7 g (0.3 mol) of 4-chlorobutyl 3-chloropropionate are added dropwise. The mixture is stirred at this temperature for a further 4 hours.

For work-up, the reaction mixture is cooled to 50° C., and 200 ml of xylene are added. The mixture is washed at this temperature once with 300 ml of water, once with 150 ml of water and a further twice with 25 ml of water. The organic phase is subsequently evaporated under reduced pressure, and the resultant crude product is recrystallized from isopropanol (50 ml).

Yield: 37.6 g (78% of theory).

EXAMPLE 4

Preparation of 3-Chloropropyl 3-Chloropropionate 101.5 ml (129.6 g, 1.00 mol) of 3-chloropropionyl chloride are added dropwise over about 30 minutes, at 90° C., to 86.1 ml of 3-chloro-1-propanol (97.4 g, 1.00 mol). During the addition, spontaneous evolution of gas occurs, and the reaction temperature drops to about 70° C. When the addition is complete, the reaction mixture is again heated to 100° C. and stirred at this temperature for a further 30 minutes. After cooling, the resultant crude product is purified by distillation.

Yield: 186.4 g (98% of theory).

EXAMPLE 5

Preparation of Hydroquinone bis[4-(3-Acryloyloxypropoxy)benzoate] from 3-Chloropropyl 3-Chloropropionate 193.2 g (1.40 mol) of potassium carbonate, 8.3 g (0.05 mol) of potassium iodide and 0.3 g of 2,6-di-t-butyl-4-(N,N-dimethylaminomethyl)phenol as stabilizer are suspended in 230 ml of N-methyl-2-pyrrolidinone, and the mixture is heated to 60° C. At this temperature, 70.1 g (0.20 mol) of hydroquinone bis(4-hydroxybenzoate) are added. The mixture is subsequently warmed further to 95° C. When this temperature has been reached, 92.6 g (0.48 mol) of 3-chloropropyl 3-chloropropionate are added dropwise over the course of 15 minutes. The mixture is then stirred at 95° C. for a further 5 hours.

For work-up, the mixture is cooled to 80° C., and 200 ml of xylene are added. The mixture is washed at this temperature once with 270 ml of water, once with 180 ml of water and a further twice with 40 ml of water. The organic phase is subsequently dried by azeotropic distillation of about 50 ml of xylene in a partial vacuum. The clean product crystallizes out on cooling to 15° C. This is filtered off and washed with EtOH.

Yield: 76.0 g (62% of theory).

EXAMPLE 6

Preparation of (4-Acryloyloxybutoxy)phenol 4-Allyloxybenzoate from 4-Chlorobutyl-3-chloropropionate 162.1 g (1.0 mol) of potassium carbonate, 3.3 g (20 mmol) of potassium iodide and 0.2 g (0.8 mmol) of 2,6-di-t-butyl-4-(N,N-dimethylaminomethyl)phenol as stabilizer are suspended in 150 ml of N-methyl-2-pyrrolidinone. 54.0 g (0.2 mol) of hydroquinone 4-allyloxybenzoate are subsequently added with good stirring. When the reaction temperature of 100° C. has been reached, 79.6 g (0.4 mol) of 4-chlorobutyl 3-chloropropionate are added dropwise. The mixture is stirred at this temperature for a further 4 hours.

For work-up, the mixture is cooled to 80° C., and 110 ml of xylene are added. The mixture is washed at this temperature once with 300 ml of water, once with 200 ml of water, once with 100 ml of water, once with 100 ml of 10% strength sodium hydroxide solution and twice again with 150 ml of water. The organic phase is subsequently dried by azeotropic distillation of 30 ml of xylene in a partial vacuum. The hydroquinone bis-4-allyloxybenzoate formed as byproduct is filtered off after cooling to 50° C. The product crystallizes out at 0° C. after addition of 100 ml of ethanol.

Yield: 32.9 g (38% of theory).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A one-step process for the preparation of acryloyl group-containing liquid-crystalline monomers of the general formula (1)

$$(Z-Y^1-A^2-Y^2-)_m M(-O-A^1\text{-acrylate})_n \quad (1)$$

comprising reacting mesogenic alcohols of the general formula (2)

$$(Z-Y^1-A^2-Y_2-)_m M(OH)_n \quad (2)$$

with esters of 3-chloropropionic acid of the general formula (3)

$$ClPr-A^1-X \quad (3)$$

with elimination of HCl, where acrylate is an acrylate radical,

ClPr is a 3-chloropropionate radical, $A^1$ are identical or different alkyl chain spacers having 2–20 carbon atoms, in which the carbon chain may be interrupted by non-adjacent ether, thioether, or imino groups, $A^2$ are radicals $A^1$ or single chemical bonds, M is a mesogenic group, X is a leaving group, Z are alkyl radicals or crosslinkable groups, $Y^1$ and $Y^2$, independently of one another, are a single chemical bond, —O—, —S—, —O—CO—, —CO—O—, —O—CO—O, —CO—NR$^1$—, —NR$^1$—CO—, —O—CO—NR$^1$—, —NR$^1$—CO—O— or —NR$^1$—CO—NR$^1$—, $R^1$ is hydrogen or a $C_1$–$C_4$-alkyl radical, n has a value of 1, 2, 3 or 4, and m has a value of 0, 1, 2 or 3.

2. A process as claimed in claim 1, wherein n is 2.

3. A process as claimed in claim 1, wherein m is 0.

4. A process as claimed in claim 2, wherein m is 0.

5. A process as claimed in claim 1, wherein M is a radical of the general formula (4)

$$(-T-Y^3)_r-T- \quad (4)$$

in which

T are independently divalent saturated or unsaturated, isocyclic or heterocyclic, substituted or unsubstituted hydrocarbon radicals having 5–20 carbon atoms, $Y^3$ is a single chemical bond, —O—, —S—, —O—CO—, —CO—O—, —O—CO—O—, —CO—NR$^2$—, —NR$^2$—CO—, —O—CO—NR$^2$—, —NR$^2$—CO—O—, —NR$^2$—CO—NR$^2$—, —CH$_2$—O—, —O—CH$_2$—, —CH=N—, —N=CH— or —N=N—, $R^2$ is hydrogen or a $C_1$–$C_4$-alkyl radical, and r is 0, 1, 2, 3 or 4.

6. A process as claimed in claim 3, wherein M is a radical of the general formula (4)

$$(-T-Y^3)_r-T- \quad (4)$$

in which

T are independently divalent saturated or unsaturated, isocyclic or heterocyclic, substituted or unsubstituted hydrocarbon radicals having 5–20 carbon atoms, $Y^3$ is a single chemical bond, —O—, —S—, —O—CO—, —CO—O—, —O—CO—O—, —CO—

NR²—, —NR²—CO—, —O—CO—NR²—, —NR²—CO—O—, —NR²—CO—NR²—, —CH₂—O—, —O—CH₂—, —CH=N—, —N=CH— or —N=N—,

R² is hydrogen or a C₁–C₄-alkyl radical, and r is 0, 1, 2, 3 or 4.

7. A process as claimed in claim 1, wherein the mesogenic groups M conform to optionally substituted structural formulae (5) or (6)

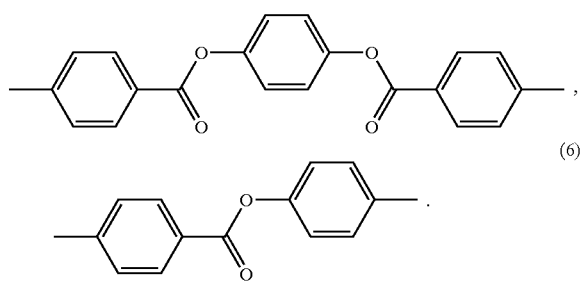

(5)

(6)

8. A process as claimed in claim 3, wherein the mesogenic groups M conform to optionally substituted structural formulae (5) or (6)

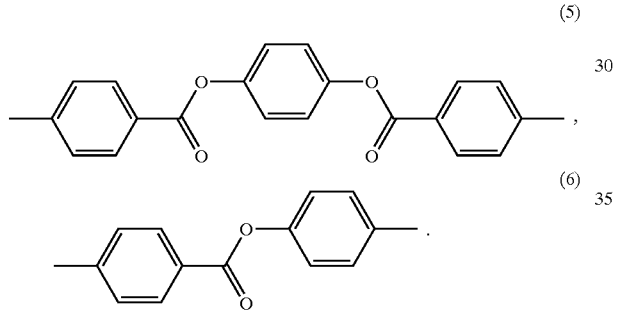

(5)

(6)

9. A process as claimed in claim 1, wherein only one compound of the general formula (3) is employed.

10. A process as claimed in claim 2, wherein only one compound of the general formula (3) is employed.

11. A process as claimed in claim 3, wherein only one compound of the general formula (3) is employed.

12. A process as claimed in claim 5, wherein only one compound of the general formula (3) is employed.

13. A process as claimed in claim 7, wherein only one compound of the general formula (3) is employed.

14. A process as claimed in claim 1, wherein X is halogen or a sulfonic acid derivative.

15. A process as claimed in claim 2, wherein X is halogen or a sulfonic acid derivative.

16. A process as claimed in claim 3, wherein X is halogen or a sulfonic acid derivative.

17. A process as claimed in claim 5, wherein X is halogen or a sulfonic acid derivative.

18. A one-step process for the preparation of acryloyl group-containing liquid-crystalline monomers of the general formula (1)

$$(Z-Y^1-A^2-Y^2-)_mM(-O-A^1\text{-acrylate})_n \qquad (1)$$

comprising reacting mesogenic alcohols of the general formula (2)

$$(Z-Y^1-A^2-Y^2-)_mM(OH)_n \qquad (2)$$

with esters of 3-chloropropionic acid of the general formula (3)

$$ClPr-A^1-X \qquad (3)$$

with elimination of HCl, where acrylate is an acrylate radical,

ClPr is a 3-chloropropionate radical,

A¹ are identical or different alkyl chain spacers having 2–20 carbon atoms, in which the carbon chain may be interrupted by non-adjacent ether, thioether, or imino groups, A² are radicals A¹ or single chemical bonds, M is a mesogenic group, X is a leaving group, Z are alkyl radicals or crosslinkable groups, Y¹ and Y², independently of one another, are a single chemical bond, —O—, —S—, —O—CO—, —CO—O—, —O—CO—O, —CO—NR¹—, —NR¹—CO—, —O—CO—NR¹—, —NR¹—CO—O— or —NR¹—CO—NR¹—, R¹ is hydrogen or a C₁–C₄-alkyl radical, n has a value of 1 or 2, m has a value of 0, 1, 2 or 3.

19. A process as claimed in claim 18, wherein m is 0.

20. A process as claimed in claim 18, wherein M is a radical of the general formula (4)

$$(-T-Y^3-)_r-T- \qquad (4)$$

in which

T are independently divalent saturated or unsaturated, isocyclic or heterocyclic, substituted or unsubstituted hydrocarbon radicals having 5–20 carbon atoms, Y³ is a single chemical bond, —O—, —S—, —O—CO—, —CO—O—, —O—CO—O—, —CO—NR²—, —NR²—CO—, —O—CO—NR²—, —NR²—CO—O—, —NR²—CO—NR²—, —CH₂—O—, —O—CH₂—, —CH=N—, —N=CH— or —N=N—, R² is hydrogen or a C₁–C₄-alkyl radical, and r is 0, 1, 2, 3 or 4.

* * * * *

UNITED STATES PATENT AND TRADEMARK OFFICE
CERTIFICATE OF CORRECTION

PATENT NO.    : 6,440,328 B1
DATED         : August 27, 2002
INVENTOR(S)   : Volker Stanjek et al.

It is certified that error appears in the above-identified patent and that said Letters Patent is hereby corrected as shown below:

Column 8,
Line 10, delete "$Y_2$" and insert therefor -- $Y^2$ --.

Signed and Sealed this

Fourth Day of February, 2003

JAMES E. ROGAN
*Director of the United States Patent and Trademark Office*